United States Patent [19]

Melloni et al.

[11] 4,078,073
[45] Mar. 7, 1978

[54] N-TRICYCLIC DERIVATIVES OF AZETIDINE

[75] Inventors: Piero Melloni, Milan; Arturo Della Torre, Varese; Francesco Lauria, Milan; Norina Passerini, Milan; Alessandro Rossi, Milan; Raffaele Tommasini, Milan, all of Italy

[73] Assignee: Carlo Erba S.p.A., Milan, Italy

[21] Appl. No.: 738,373

[22] Filed: Nov. 2, 1976

Related U.S. Application Data

[62] Division of Ser. No. 647,980, Jan. 9, 1976.

[30] Foreign Application Priority Data

Jan. 24, 1975 Italy .................................. 19535/75

[51] Int. Cl.² .......................................... C07D 313/12
[52] U.S. Cl. .................................. 424/278; 260/333; 260/239 A; 260/327 B; 424/244; 424/275
[58] Field of Search ........................ 260/333; 424/278

[56] References Cited

U.S. PATENT DOCUMENTS 3,509,176  4/1970  Winter et al. .................... 260/333
3,991,103  11/1976  Barton et al. .................... 260/333

Primary Examiner—Norma S. Milestone
Attorney, Agent, or Firm—Cushman, Darby & Cushman

[57] ABSTRACT

Novel N-tricyclic derivatives of azetidine of the formula:

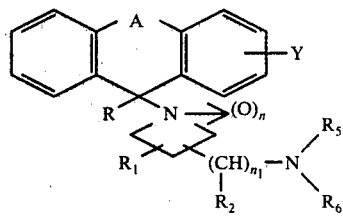

wherein A is a —CH$_2$—O— or an —O—CH$_2$ group, and the remaining substituents being defined in the specification are disclosed. An illustrative compound is 1-[11-(6,11-dihydro-dibenzo [b,e] oxepinyl)]-3-methylamino-azetidine. The compounds are useful for their anti-depressant, anti-convulsant and anxiolytic activities.

16 Claims, No Drawings

N-TRICYCLIC DERIVATIVES OF AZETIDINE

This is a division, of application Ser. No. 647,980 filed Jan. 9, 1976.

The present invention relates to N-tricyclic derivatives of azetidine, a process for their preparation and pharmaceutical compositions containing them.

The N-tricyclic derivatives of azetidine, object of the invention, have the following general formula (I)

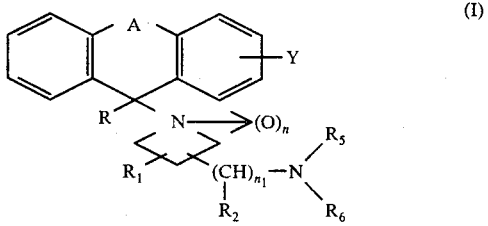

(I)

wherein

A is a $C_1$-$C_3$ alkylene group, which may optionally be substituted by one or more $C_1$-$C_4$ alkyl groups; a $C_2$-$C_3$ alkenylene group; a cyclopropylene group; or a —$CH_2$—B— or —B—$CH_2$— group, wherein B is an oxygen or sulphur atom; each of R, $R_1$ and $R_2$ groups, being the same of different, is a hydrogen atom or a $C_1$-$C_6$ alkyl group;

Y is a hydrogen atom; a $C_1$-$C_6$ alkyl group; a halogen atom; a trifluoromethyl group; an —$OR_3$ group, wherein $R_3$ is hydrogen or $C_1$-$C_6$ alkyl; or a —$SO_2R_4$ group, wherein $R_4$ is $C_1$-$C_6$ alkyl or an amino group optionally substituted by one or two $C_1$-$C_6$ alkyl groups;

$n$ is zero or 1;

$n_1$ is zero, 1 or 2;

each of $R_5$ and $R_6$ groups, being the same or different, is (a) hydrogen; (b) formyl; (c) a $C_1$-$C_6$ alkyl, a $C_2$-$C_6$ alkenyl or $C_2$-$C_6$ alkynyl group, wherein the alkyl, alkenyl and alkynyl groups may be optionally substituted by one or more substituents selected from the group consisting of halogen, $C_1$-$C_6$ alkoxy, $C_3$-$C_7$ cycloalkyl, amino optionally substituted by one or two $C_1$-$C_6$ alkyl groups, phenyl optionally substituted by one or more Y radicals, wherein Y is as defined above; (d) a $C_2$-$C_6$ alkanoyl group, wherein the alkyl chain may be optionally substituted by one or more substituents selected from the group consisting of halogen, $C_1$-$C_6$ alkoxy, amino optionally substituted by one or two $C_1$-$C_6$ alkyl group, phenyl optionally substituted by one or more Y radicals, wherein Y is as defined above; or (e) $R_5$ and $R_6$, taken together with the nitrogen atom, are a pentatomic or hexatomic monoheterocyclic radical optionally containing another heteroatom selected from the group consisting of oxygen and nitrogen, which radical may be optionally substituted by one or more $C_1$-$C_6$ alkyl groups, which in turn may be optionally substituted by one or more substituents selected from the group consisting of hydroxy, $C_1$-$C_6$ alkoxy and amino, which is optionally substituted by one or two $C_1$-$C_6$ alkyl groups, provided that, when $n_1$ is zero, the

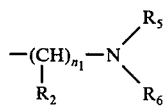

radical is exclusively bound to the carbon atom in the 3-position of the azetidine radical.

Object of the invention are also the pharmaceutical acceptable salts of the compounds of formula (I) as well as all the possible stereoisomers and the mixtures thereof. The alkyl, alkenyl, alkynyl and alkoxy groups may be either branched or straight chain groups.

When A is a $C_1$-$C_3$ alkylene group, it is preferably —$CH_2$—$CH_2$—, while when A is a $C_2$-$C_3$ alkenylene group, it is preferably vinylene. R, $R_1$ and/or $R_2$, being the same or different, are preferably hydrogen or methyl, $n$ is preferably zero, $n_1$ is preferably zero or 1. When $R_5$ and $R_6$, taken together with the nitrogen atom, are an optionally substituted monoheterocyclic radical, as hereabove said, the monoheterocyclic radical is preferably piperidino, morpholino, piperazin-1-yl or pyrrolidin-1-yl. $R_5$ and $R_6$, being the same or different, are preferably hydrogen or $C_1$-$C_4$ alkyl, in particular methyl or ethyl. Preferably, $R_5$ is hydrogen and $R_6$ is $C_1$-$C_4$ alkyl, in particular methyl or ethyl. Y is preferably hydrogen, halogen, methoxy, trifluoromethyl or methylsulphonyl.

When $n$ is 1 or 2, the

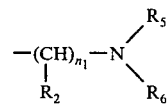

radical is preferably bound to the carbon atom in the 3-position of the azetidine radical.

Especially preferred compounds of the invention are the compounds of formula (I), wherein A is ethylene, vinylene, cyclopropylene, —$CH_2$—B— or —B—$CH_2$—, wherein B is as defined above; Y is hydrogen, fluorine, chlorine, methoxy, trifluoromethyl or methylsulphonyl; R is hydrogen; $R_1$ is hydrogen or methyl; $n$ is zero; $n_1$ is zero; $R_5$ is hydrogen and $R_6$ is $C_1$-$C_4$ alkyl, in particular methyl or ethyl. Examples of pharmaceutically acceptable salts of the compounds of formula (I) are those with hydrochloric, citric and tartaric acid.

The compounds object of the present invention are prepared according to the following method comprising:

a. the reaction of a compound of general formula (II)

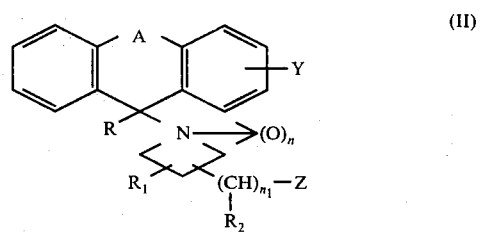

(II)

wherein

A, R, $R_1$, $R_2$, $n$, $n_1$ and Y are as defined above, Z is a halogen atom or the residue of an active ester of an alcohol, and wherein, when $n_1$ is zero, Z is exclusively bound to the carbon atom in the 3-position of the azetidine radical, with a compound of general formula (III)

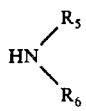 (III)

wherein
R$_5$ and R$_6$ are as defined above, or with a reactive derivative thereof, thus obtaining compounds of general formula (I) wherein, when n$_1$ is zero, the

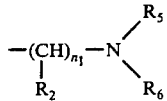

radical is exclusively bound to the carbon atom in the 3-position of the azetidine radical;

b. the reduction of a compound of general formula (II), wherein A, R, R$_1$, R$_2$ and Y are as defined above, n is zero, n$_1$ is zero or 1 and Z is a cyano group or the

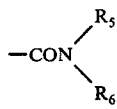

radical, wherein R$_5$ and R$_6$ are as defined above, except formyl and C$_2$-C$_6$ alkanoyl, thus obtaining compounds of general formula (I) wherein n is zero, n$_1$ is 1 or 2 and R$_5$ and R$_6$ are as defined above, except formyl and C$_2$-C$_6$ alkanoyl;

c. the reductive amination of a compound of formula (II) wherein A, R, R$_1$, R$_2$, n and Y are as defined above, n$_1$ is zero or 1 and Z is the —COR$_2$ radical, wherein R$_2$ is as defined above, so obtaining compounds of formula (I) wherein n$_1$ is 1 or 2, and R$_5$ and R$_6$ are as defined above, except formyl and C$_2$-C$_6$ alkanoyl;

and, if desired, converting a compound of formula (I) into another compound of formula (I) and/or, if desired, resolving a mixture of the optical isomers into the different isomers, and/or, if desired, salifying a compound of formula (I) with a pharmaceutically acceptable acid.

When in the compound of formula (II), Z is the residue of an active ester of an alcohol, it is preferably —O—mesyl or —O—tosyl; when Z is halogen, it is preferably bromine or chlorine.

A reactive derivative of the compound of formula (III) is for example a salt thereof, preferably with an alkaline metal.

The reaction between the compound of formula (II), wherein Z is the residue of an active ester of an alcohol or a halogen atom, and the compound of formula (III) may take place either in presence of solvents, such as dimethylformamide, dimethylacetamide, dimethylsulphoxide or mixtures of these solvents with water or in absence of solvents, when the compound of formula (III) is liquid or low-melting, at temperatures ranging between approximately 25° C and approximately 120° C.

When in the compound of formula (III) R$_5$ and/or R$_6$ are formyl or an optionally substituted C$_2$-C$_6$ alkanoyl group, the reaction between the compound of formula (II) and the compound of formula (III) may take place either in the above-cited solvents, provided they be anhydrous, or in benzene or toluene, after the salt, for example an alkaline salt, in particular a sodium salt, of the compound of formula (III) has been prepared by reaction of the compound of formula (III) with a metal, for instance an alkaline metal, or with a hydride thereof.

The reduction of the compound of formula (II) wherein Z is a cyano group or a

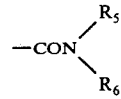

radical, takes preferably place with a mixed hydride, such as for instance, lithium alluminium hydride, or with diboran, preferably in organic solvents, such as tetrahydrofuran, ethyl ether or diglyme.

The reductive amination of the compound of formula (II), wherein Z is the —COR$_2$ radical, wherein R$_2$ is as defined above, may be performed in a conventional manner by reaction with a compound having the above-indicated formula (III), wherein R$_5$ and R$_6$ are as above-defined, except formyl or C$_2$-C$_6$ alkanoyl, following, for instance, Leuckart's method in presence of formic acid, or with sodium borohydride. In this case, compounds of formula (I), wherein R$_5$ and R$_6$ are as defined above, except formyl and C$_2$-C$_6$ alkanoyl, are obtained. The reductive amination may be also carried out, without using the compound of formula (III), with sodium borohydride and ammonium acetate, according to what described in J. Med. Chem. 17, 358 (1974), so obtaining compounds of formula (I) wherein R$_5$ and R$_6$ are hydrogen. The method described in said publication allows to maintain the eventual N-oxide function present in the compound of formula (II) unchanged.

As hereabove stated, a compound of formula (I) may be converted into another compound of formula (I) working according to the usual methods of organic chemistry.

Thus, or example, a compound of formula (I) wherein R$_5$ and/or R$_6$ are hydrogen, may be converted into a compound of formula (I) wherein R$_5$ and/or R$_6$ are formyl or optionally substituted C$_2$-C$_6$ alkanoyl as hereabove stated by acylation in the usual reaction conditions for instance with the halide of an acid or with a simple or mixed anhydride, the latter one prepared for instance in organic solvents, such as chloroform, tetrahydrofuran, by reaction of a carboxylic acid with ethyl chloroformate in presence of triethylamine.

When the acylation is carried out with the halide of an acid, alkaline hydroxides or carbonates are used as acceptors of the hydrohalic acid forming in the reaction. A compound of formula (I) wherein n is zero, R$_5$ is alkyl and R$_6$ is hydrogen may be converted into a compound of formula (I) wherein n is zero and R$_5$ and R$_6$ are alkyl, for instance by acylation according to the above-described methods and subsequent reduction of the amide to an amine, for example, with a mixed hydride such as lithium alluminum hydride or with diboran, preferably in solvents such as tetrahydrofuran, ethyl ether or diglime, or by alkylation for example with a sulphate or an alkyl halide or by reductive alkylation with an aldehyde using e.g. sodium borohydride.

If, starting from a compound wherein R$_5$ and R$_6$ are hydrogen, compounds are intended to be obtained, wherein R$_5$ is hydrogen and R$_6$ is C$_1$-C$_6$ alkyl, a compound of formula (I) wherein R$_5$ is hydrogen and R$_6$ is formyl or C$_2$-C$_6$ alkanoyl, obtained as hereabove described, may be reduced, for example, with a mixed hydride, e.g. lithium alluminium hydride, or it is possible to prepare an acyl derivative, the tosyl derivative or the trifluoroacetyl derivative of the amine, to alkylate the amine with a sulphate or with an alkyl halide and subsequently to remove the three above-mentioned groups by alkaline or acid hydrolysis, according to known methods. If the free amino group is intended to be methylated into a compound of formula (I), it is possible to reduce, by means of the usual methods, for instance with lithium alluminium hydride in tetrahydrofuran, the carbamate prepared by treatment of the amine with ethyl chloroformate in solvents such as chloroform or methylene chloride and in presence of a base, such as for instance an alkaline hydroxide. Also the optional salification step as well as the resolution of a mixture of optical isomers may be carried out following the usual methods of organic chemistry.

The compounds of formula (II) wherein $n_1$ is zero and Z is a residue of an active ester of an alcohol or a halogen atom, being Z bound to the carbon atom in the 3-position of the azetidine radical, are prepared according to what described in J. Org. Chem. 32, 2972 (1967) or J. Org. Chem. 37, 3953 (1972), starting from compounds of formula

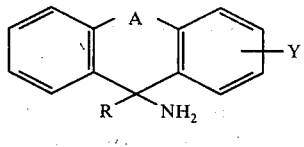

wherein

A, R and Y are as defined above which may be prepared in turn according to the techniques described in J. Med. Chem. 6, 255 (1963); Ber. 58, 1439 (1925); Chem. Abstr. 70, 11583; Chem. Abstr. 66, 2426a; J. Het. Chem. 4, 645 (1967).

The compounds of formula (II) wherein $n_1$ is zero and Z is one of the —CN or

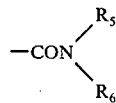

groups, wherein $R_5$ and $R_6$ are as defined above except formyl and $C_2$-$C_6$ alkanoyl, and the Z group is bound to the carbon atom in the 2-position of the azetidine radical, are obtained, with known reactions, from the corresponding carboxylic ester which is in turn directly obtained when forming the azetidine ring as described in J. Het. Chem. 8, 795 (1973).

The compounds of formula (II) wherein $n_1$ is zero and Z is one of the —CN or

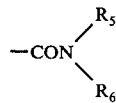

groups, wherein $R_5$ and $R_6$ are as defined above, except formyl and $C_2$-$C_6$ alkanoyl, and the Z group is bound to the carbon atom in the 3-position of the azetidine radical, are obtained starting from compounds of formula (II) wherein $n_1$ is zero and Z is the residue of an active ester of an alcohol or a halogen atom, for example, reacting the halogen derivative with an alkaline cyanide in water/acetone or dimethylformamide, thus obtaining the corresponding nitrile which may be then converted, through known reactions, into the amide.

The compounds of formula (II) wherein $n_1$ is 1 and Z is one of the —CN or

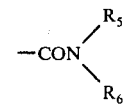

groups, which may be bound either to the carbon atom in the 2-position or to the carbon atom in the 3-position of the azetidine radical, are prepared in an analogous way.

The compounds of formula (II) wherein $n_1$ is 1 and Z is the residue of an active ester or a halogen atom, are prepared starting from the compounds of formula (II) wherein $n_1$ is zero and Z is preferably a cyano group, when same is bound to the carbon atom in the 3-position of the azetidine ring, or Z is preferably an alkoxy-carbonyl group, when same is bound to the carbon atom in the 2-position of the azetidine ring, by conversion, through known reactions, of the cyano or alkoxycarbonyl group into a primary alcohol and subsequent conversion of the hydroxy group so obtained in an active ester, for instance by reaction with methane sulphonylchloride in pyridine at 0° C, or in a halogen atom, for instance by reaction with a phosphorus oxyhalide.

The compounds of formula (II) wherein Z is a —COR$_2$ radical, wherein R$_2$ is hydrogen or $C_1$-$C_6$ alkyl and wherein $n_1$ is zero or 1 when Z is bound to the carbon atom in the 3-position of the azetidine radical, while $n_1$ is exclusively 1 when Z is bound to the carbon atom in the 2-position of the azetidine radical, are prepared starting from the corresponding compounds of formula (II) wherein Z is the residue of an active ester of an alcohol or a halogen atom by reaction with 1,3-dithianes according to Corey and Seebach's method (Angew. Chem. Intern. Ed. 4, 1075 (1965)).

The compounds of formula (II) wherein $n_1$ is 1, Z is —CHO and the

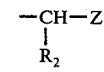

radical is bound to the carbon atom in the 3-position of the azetidine ring, may be also obtained starting from the corresponding compounds of formula (II) wherein n is zero and wherein Z is the residue of an active ester of an alcohol or a halogen atom by reaction with 1,3-oxazines according to Meyer's method (J. Am. Chem. Soc. 91, 763, 2155, 5887 (1969)).

The compounds of formula (II) wherein $n_1$ is 2 and Z is the residue of an active ester of an alcohol or a halogen atom are obtained by reaction of a compound of formula (II), wherein $n_1$ is zero and Z is the residue of an active ester of an alcohol or a halogen atom, with an ester of the malonic acid, thus obtaining a compound of formula (II) wherein $n_1$ is 1 and Z is a carboxylic group, which, after reduction to alcohol by known methods, may be converted, through known reactions as seen hereabove, into a compound wherein Z is the residue of an active ester of an alcohol or a halogen atom and $n_1$ is 2.

The other functional groups may be obtained from the acid by means of reactions known to those skilled in the art.

The compounds of the present invention have shown to be remarkably active on the central nervous system as antidepressant and anticonvulsant agents, and in some cases, also as anxiolytic agents.

The antidepressant activity was evaluated in mice on the basis of the prevention of reserpine-induced blepharospasm and hypothermia.

Reserpine was administered endoperitoneally at a dosage of 2.5 mg/kg, and the tested compounds were orally administered 30 minutes before the administration of reserpine. Recording of blepharospasm (evaluated in scores according to the technique described by Rubin B. et al. in J. Pharmacol. 120, 125, 1957) and measurement by body temperature (by means of a rectal thermocouple) were taken an hour, and respectively, four hours after the administration of reserpine. The anticonvulsant activity was evaluated in mice on the basis of the prevention of pentylenemetrazole-induced convulsions.

Pentylenemetrazole was endoperitoneally administered at a dosage of 130 mg/kg, while the tested compounds were administered orally 30 minutes before the administration of the convulsant agent.

The compounds object of the present invention have furthermore proved to be little toxic. As concerns in particular the compounds provided with anticonvulsant activity, it has to be noted that the difference between doses active on pentylenemetrazole-induced convulsions and doses able to cause modifications of some degree on the central nervous system or nervous vegetative system in comparison with known drugs with analogous activity is great, while as concerns the compounds with antidepressant activity, they have shown to be not only less toxic in general if compared with standard antidepressant agents but also less toxic on the heart and unprovided with peripheral atropinic effects.

The compounds of the present invention are preferably administered orally.

The results of the clinical tests in humans have confirmed the pharmacological data.

As regards the antidepressant activity, the dosage suitable for the oral administration to adult humans of, for example, 1-[5-(10,11-dihydro-5H-dibenzo[a,d]cycloheptenyl)]-3-methyl-amino-azetidine, 1-[6-(1,1a,6,10b-tetrahydro-dibenzo[a,e]cylopropan[c]cycloheptenyl)]-3-methylamino-azetidine, 1-[11-(6,11-dihydro-dibenzo[b,e]oxepinyl)]-3-methylamino-azetidine, and 1-[11-(6,11-dihydro-dibenzo[b,e]thiepinyl)]-3-methylamino-azetidine, is preferably 20-50 mg pro dose 2-4 times a day. As regards the anticonvulsant activity, the dosage suitable for the oral administration of for example 1-[5-(10,11-dihydro-5H-dibenzo[a,d]cycloheptenyl)]-3-methylamino-azetidine is preferably 50-100 mg pro dose 3-5 times a day.

The pharmaceutical compositions containing the compounds of this invention are prepared according to conventional methods and are, for example, capsules, tablets, pills. Examples of substances containing the active principle which may be used as pharmaceutical carriers or diluents are talc, gelatine, lactose, starch, magnesium stearate as well as all other non-toxic substances used in pharmaceutical formulations.

The following examples illustrate but do not limit the present invention.

EXAMPLE 1

1-[5-(10,11-dihydro-5H-dibenzo[a,d]cycloheptenyl)]-3-mesiloxy-azetidine (2 g) was dissolved in dimethylformamide (10 ml) and 35% methylamine (12 ml). The solution was heated overnight at 45°-50° C, poured into water (100 ml), then extracted with ethyl acetate (2 × 50 ml). After drying on sodium sulphate, evaporation to dryness and solidification with petroleum ether, crystallization from n-hexane gave 1-[5-(10,11-dihydro-5H-dibenzo[a,d]cycloheptenyl)]-3-methylamino-azetidine (1.1 g; m.p. 85°-87° C). This compound (1.1 g) was dissolved in ethyl ether (20 ml), and a solution of 7% ethanolic hydrochloric acid was added, so precipitating 1-[5-(10,11-dihydro-5H-dibenzo[a,d]cycloheptenyl]-3-methylamino-azetidine dihydrochloride (1.1 g; m.p. 210°-213° C).

By proceeding analogously, the following compounds were obtained:

1-[5-(10,11-dihydro-5H-dibenzo[a,d]cycloheptenyl)]-3-amino-azetidine dihydrochloride, m.p. 163°-165° C 1-[5-(10,11-dihydro-5H-dibenzo[a,d]cycloheptenyl)]-3-dimethylamino-azetidine dihydrochloride, m.p. 180°-181° C 1-[5-(10,11-dihydro-5H-dibenzo[a,d]cyclopentyl)]-3-ethylamino-azetidine dihydrochloride, m.p. 138°-141° C 1-[5-(10,11-dihydro-5H-dibenzo[a,d]cyclopentyl)]-3-diethylamino-azetidine dihydrochloride 1-[5-(10,11-dihydro-5H-dibenzo[a,d]cycloheptenyl]-3-cyclohexylamino-azetidine dihydrochloride, m.p. 145°-147° C 1-[5-(10,11-dihydro-5H-dibenzo[a,d]cycloheptenyl)]-3-isopropylamino-azetidine dihydrochloride, m.p. 179°-181° C 1-[5-(10,11-dihydro-5H-dibenzo[a,d]cycloheptenyl)]-3-t-butylamino-azetidine dihydrochloride, m.p. 177°-179° C 1-[5-(10,11-dihydro-5H-dibenzo[a,d]cycloheptenyl)]-3-benzylamino-azetidine dihydrochloride, m.p. 178°-180° C 1-[5-(10,11-dihydro-5H-dibenzo[a,d]cycloheptenyl)]-3-dipropargylamino-azetidine dihydrochloride, m.p. 165°-167° C, 1-[5-(3-chloro-10,11-dihydro-5H-dibenzo[a,d]cycloheptenyl)]-3-methylamino-azetidine dihydrochloride 1-[5-(3-fluoro-10,11-dihydro-5H-dibenzo[a,d]cycloheptenyl)]-3-methylamino-azetidine dihydrochloride 1-[5-(3-trifluoromethyl-10,11-dihydro-5H-dibenzo[a,d]cycloheptenyl)]-3-methylamino-azetidine dihydrochloride 1-[5-(3-methylsulphonyl-10,11-dihydro-5H-dibenzo[a,d]cycloheptenyl)]-3-methylamino-azetidine dihydrochloride 1-[5-(3-methoxy-10,11-dihydro-5H-dibenzo[a,d]cycloheptenyl)]-3-methylamino-azetidine dihydrochloride, and besides, in analogous way, starting from the following compounds:

1-[5-(5H-dibenzo[a,d]cycloheptenyl)]-3-mesiloxy-azetidine, m.p. 96°-98° C

1-[6-(1,1a,6,10b-tetrahydro-dibenzo[a,e]cyclopropan[c]cycloheptenyl)]-3-mesiloxy-azetidine, m.p. 187°-189° C 1-[11-(6,11-dihydro-dibenzo[b,e]oxepinyl)]-3-mesiloxy-azetidine, m.p. 110°-112° C 1-[11-(2-chloro-6,11-dihydro-dibenzo[b,e]oxepinyl)]-3-mesiloxy-azetidine 1-[11-(9-chloro-6,11-dihydro-dibenzo[b,e]oxepinyl)]-3-mesiloxy-azetidine
1-[11-(2-trifluoromethyl-6,11-dihydro-dibenzo[b,e]oxepinyl)]-3-mesiloxy-azetidine
1-[11-(9-trifluoromethyl-6,11-dihydro-dibenzo[b,e]oxepinyl)]-3-mesiloxy-azetidine
1-[11-(2-methoxy-6,11-dihydro-dibenzo[b,e]oxepinyl)]-3-mesiloxy-azetidine
1-[11-(9-methoxy-6,11-dihydro-dibenzo[b,e]oxepinyl)]-3-mesiloxy-azetidine
1-[11-(2-methylsulphonyl-6,11-dihydro-dibenzo[b,e]oxepinyl)]-3-mesiloxy-azetidine
1-[11-(9-methylsulphonyl-6,11-dihydro-dibenzo[b,e]oxepinyl)]-3-mesiloxy-azetidine
1-[11-(6,11-dihydro-dibenzo[b,e]thiepinyl)]-3-mesiloxy-azetidine
1-[11-(2-chloro-6,11-dihydro-dibenzo[b,e]thiepinyl)]-3-mesiloxy-azetidine
1-[11-(9-chloro-6,11-dihydro-dibenzo[b,e]thiepinyl)]-3-mesiloxy-azetidine
1-[11-(2-trifluoromethyl-6,11-dihydro-dibenzo[b,e]thiepinyl)]-3-mesiloxy-azetidine
1-[11-(9-trifluoromethyl-6,11-dihydro-dibenzo[b,e]thiepinyl)]-3-mesiloxy-azetidine
1-[11-(2-methoxy-6,11-dibenzo[b,e]thiepinyl)]-3-mesiloxy-azetidine
1-[11-(9-methoxy-6,11-dibenzo[b,e]thiepinyl)]-3-mesiloxy-azetidine
1-[11-(2-methylsulphonyl-6,11-dibenzo[b,e]thiepinyl)]-3-mesiloxy-azetidine
1-[11-(9-methylsulphonyl-6,11-dibenzo[b,e]thiepinyl)]-3-mesiloxy-azetidine
1-{9-[9,10-dihydro-(10,10-dimethyl)-antracenyl[}•mesiloxy-azetidine, the following compounds were prepared:
1-[5-(5H-dibenzo[a,d]cycloheptenyl)]-3-methylamino-azetidine, m.p. 156°–159° C
1-[6-(1,1a,6,10b-tetrahydro-dibenzo[a,e]cyclopropan[c]cycloheptenyl)]-3-methylamino-azetidine, m.p. 98°–100° C
1-[11-(6,11-dihydro-benzo[b,e]oxepinyl)]-3-methylamino-azetidine, m.p. 61°–64° C
1-[11-(2-chloro-6,11-dihydro-dibenzo[b,e]oxepinyl)]-3-methylamino-azetidine
1-[11-(9-chloro-6,11-dihydro-dibenzo[b,e]oxepinyl)]-3-methylamino-azetidine
1-[11-(2-trifluoromethyl-6,11-dihydro-dibenzo[b,e]oxepinyl)]-3-methylamino-azetidine
1-[11-(9-trifluoromethyl-6,11-dihydro-dibenzo[b,e]oxepinyl)]-3-methylamino-azetidine
1-[11-(2-methoxy-6,11-dihydro-dibenzo[b,e]oxepinyl)]-3-methylamino-azetidine
1-[11-(9-methoxy-6,11-dihydro-dibenzo[b,e]oxepinyl)]-3-methylamino-azetidine
1-[11-(2-methylsulphonyl-6,11-dihydro-dibenzo[b,e]oxepinyl)]-3-methylamino-azetidine
1-[11-(9-methylsulphonyl-6,11-dihydro-dibenzo[b,e]oxepinyl)]-3-methylamino-azetidine
1-[11-(6,11-dihydro-dibenzo[b,e]thiepinyl)]-3-methylamino-azetidine
1-[11-(2-chloro-6,11-dihydro-dibenzo[b,e]thiepinyl)]-3-methylamino-azetidine
1-[11-(9-chloro-6,11-dihydro-dibenzo[b,e]thiepinyl)]-3-methylamino-azetidine
1-[11-(2-trifluoromethyl-6,11-dihydro-dibenzo[b,e]thiepinyl)]-3-methylamino-azetidine
1-[11-(9-trifluoromethyl-6,11-dihydro-dibenzo[b,e]thiepinyl)]-3-methylamino-azetidine
1-[11-(2-methoxy-6,11-dihydro-dibenzo[b,e]thiepinyl)]-3-methylamino-azetidine
1-[11-(9-methoxy-6,11-dihydro-dibenzo[b,e]thiepinyl)]-3-methylamino-azetidine
1-[11-(2-methylsulphonyl-6,11-dihydro-dibenzo[b,e]thiepinyl)]-3-methylamino-azetidine
1-[11-(9-methylsulphonyl-6,11-dihydro-dibenzo[b,e]thiepinyl)]-3-methylamino-azetidine
1-{9-[9,10-dihydro-(10,10-dimethyl)-antracenyl]}-3-methylamino-azetidine.

The compound 1-[5-(10,11-dihydro-5H-dibenzo[a,d]cycloheptenyl)]-3-mesiloxy-azetidine used as starting material for the preparation of the compound 1-[5-(10,11-dihydro-5H-dibenzo[a,d]cycloheptenyl)]-3-methylamino-azetidine, was prepared in the following way:

Dibenzosuberone oxime, (89 g) prepared according to J. Med. Chem. 6, 255 (1963), was refluxed for four hours with 85% powder zinc (140.5 g), ammonium acetate (16 g), 99% ethanol (400 ml) and concentrated ammonium hydroxide (1950 ml). After filtration, exhaustively washing of the solid product with 50% sodium hydroxide, extraction with ethyl ether, drying on sodium sulphate and evaporation to dryness, 5-amino-10,11-dihydro-5H-dibenzo[a,d]-cycloheptene (65 g; m.p. 89°–91° C) crystallized from cyclohexane. A solution consisting of 5-amino-10,11-dihydro-5H-dibenzo[a,d]-cycloheptene (32 g), epichlorhydrine (12 ml) and methanol (180 ml) was first allowed to rest for three days in a 500 ml flask, then refluxed for three days again. After evaporation to dryness, an oil was obtained which was taken up with acetone (250 ml). Thus, a solid product precipitated, and by cooling 1-[5-(10,11-dihydro-5H-dibenzo[a,d]cycloheptenyl)]-3-azetidinol hydrochloride (15.3 g) crystallized, m.p. 158°–161° C. The remaining acetone solution was evaporated to dryness, the residue was taken up with methanol (80 ml) and refluxed overnight, then evaporated to dryness again. The resulting oil was taken up again with acetone (150 ml) so as to recover 6.5 g again of the hydrochloride of the above compound. The hydrochloride was shaken with 25% sodium hydroxide (250 ml) and ethyl ether (300ml), the ether was removed and then the aqueous phase extracted two times again with ethyl ether. After washing with water, drying (Na$_2$SO$_4$) and evaporation to dryness, 1-[5-(10,11-dihydro-5H-dibenzo[a,d]cycloheptenyl)]-3-azetidinol (15.2 g; m.p. 121°–127° C) was obtained. 1-[5-(10,11-dihydro-5H-dibenzo[a,d]cycloheptenyl)[-3-azetidinol (14 g) was dissolved in anhydrous pyridine (104 ml). Methane sulphochloride (6.12 ml) was added dropwise under stirring at −20° C, and the stirring at −20° C was maintained for an hour.

The solution was allowed to rest overnight at 0° C, then poured into water and ice (1000 ml). Filtration and crystallization from isopropyl ether and little benzene gave 1-[5-(10,11-dihydro-5H-dibenzo[a,d]cycloheptenyl)]-3-mesiloxy-azetidine (12.1 g; m.p. 102°–104° C).

The other compounds used as starting materials for the preparation of the compounds of the present Example were prepared analogously.

EXAMPLE 2

A mixture consisting of 1-[5-(10,11-dihydro-5H-dibenzo[a,d]cycloheptenyl)]-3-methyl-3-azetidinol (5.3 g), potassium cyanide (3.5 g) and concentrated sulphuric acid (6 ) in diisopropyl ether (30 ml) was heated at 40° C under stirring for 2 hours. The mixture was then poured into water and ice, extracted with ethyl ether, washed with a solution of sodium bicarbonate, then with water, dried (Na$_2$SO$_4$) and evaporated to dryness, so to give an oil (4.1 g) which was reduced in anhydrous tetrahydrofuran with lithium alluminium hydride (1 g) at room temperature. Water (1 ml), 15% sodium hydroxide (1 ml), then water (3 ml) were added to the solution dropwise. After stirring at room temperature for half an hour, filtration, exhaustive washing with ethyl ether, drying (Na$_2$SO$_4$) and evaporation to dryness, 1-[5-(10,11-dihydro-5H-dibenzo[a,d]cycloheptenyl)]-3-methyl-3-methylamino-azetidine was obtained (1.7 g; m.p. 91°-93° C). The same compound could be prepared starting from the mesiloxy derivative obtained as described in Example 1.

The compound 1-[5-(10,11-dihydro-5H-dibenzo[a,d]cycloheptenyl)]-3-methyl-3-azetidinol used as starting material was prepared as follows:

to a solution of methyl magnesium iodide prepared starting from methyl iodide (14.2 g) and Mg (2.8 g) in ethyl ether (200 ml), 1-[5-(10,11-dihydro-5H-dibenzo[-a,d]cycloheptenyl]-azetidin-3-one (10 g; m.p. 99°-105° C), in turn prepared according to a method analogous to that one described in J. Am. Chem. Soc., 94, 7586 (1972), was added under stirring.

After the addition the mixture was diluted with a saturated aqueous solution of ammonium chloride (200 ml), subsequently extracted with ethyl ether (2 × 200 ml), dried (Na$_2$SO$_4$), and evaporated to dryness, thus remaining an oil which was crystallized from isopropyl ether to give 1-[5-(10,11-dihydro-5H-dibenzo[a,d]cycloheptenyl)]-3-methyl-3-azetidinol (5.6 g; m.p. 112°-115°).

EXAMPLE 3

1-[5-(10,11-dihydro-5H-dibenzo[a,d]cycloheptenyl)]-3-mesiloxy-azetidine (1.5 g) was dissolved in morpholine (15 ml) at 70° C and kept at this temperature for twelve hours. By pouring the solution into water and ice, a solid product was obtained, which was then filtered, washed with water and crystallized from hexane so to give 1-[5-(10,11-dihydro-5H-dibenzo[a,d]cycloheptenyl)]-3-(N-morpholino)-azetidine (1.2 g).

By proceeding analogously, all the derivatives were prepared to obtain which it is necessary to start from liquid amines, or respectively low-melting or water-soluble amines, such as piperidine, piperazine, methylpiperazine, hydroxyethylpiperazine.

EXAMPLE 4

1-[5-(10,11-dihydro-5H-dibenzo[a,d]cycloheptenyl)]-3-mesiloxy-azetidine (3.43 g) prepared according to Example 1, was dissolved in carbonium tetrachloride (30 ml) and the solution was kept at 30° C under stirring, then m-chloro-perbenzoic acid (3.5 g) was added. The solution was stirred for 48 hours, then poured into water and neutralized with sodium carbonate; the solid product obtained was filtered, then crystallized from ethyl acetate to give 1-[5-(10,11-dihydro-5H-dibenzo[-a,d]cycloheptenyl)]-3-mesiloxy-azetidine N-oxide (2.4 g).

Starting from this N-oxide compound and proceeding analogously as described in Example 1, the compound 1-[5-(10,11-dihydro-5H-dibenzo[a,d]cycloheptenyl)]-3-methylamino-azetidine, N-oxide was obtained as well as, starting from the proper N-oxide compounds, the N-oxide derivatives of the other compounds described in Example 1 were obtained.

EXAMPLE 5

To a suspension of lithium alluminium hydride (0.74 g) in anhydrous ethyl ether (40 ml), 1-[5-(10,11-dihydro-5H-dibenzo[a,d]cycloheptenyl)]-3-cyano-azetidine (5.5 g) dissolved in tetrahydrofuran (40 ml) and anhydrous ehtyl ether (60 ml) was added dropwise. The mixture was refluxed for ten hours, then water (0.74 ml), 15% sodium hydroxide (0.74 ml) and water (2.3 ml) were added. After filtration, exhaustive washing with ethyl ether and evaporation to dryness, an oil (3.3 g) was obtained. After taking up of the oil with ethyl ether, washing with water and drying (Na$_2$SO$_4$), a solution of 7% ethanolic hydrochloric acid was added, so precipitating the hygroscopic 1-[5-(10,11-dihydro-5H-dibenzo[a,d]cycloheptenyl)]-3-aminomethyl-azetidine dihydrochloride (3.6 g; m.p. 135°-140° C).

The compound 1-[5-(10,11-dihydro-5H-dibenzo[a,d]cycloheptenyl)]-3-cyano-azetidine used as starting material was prepared as follows:

To 1-[5-(10,11-dihydro-5H-dibenzo[a,d]cycloheptenyl)]-3-mesiloxy-azetidine (5.1 g), prepared according to Example 1, in dimethylformamide (30 ml), a solution of sodium cyanide (2.21 g) in water (4 ml) was added dropwise. The mixture was allowed to rest for 24 hours at 65° C, poured into water and ice, and filtered. The solid product (4 g) was then dissolved in ethyl acetate (150 ml), dried (Na$_2$SO$_4$), evaporated to dryness to give 1-[5-(10,11-dihydro-5H-dibenzo[a,d]cycloheptenyl)]-3-cyano-azetidine (3.8 g; m.p. 162°-165° C).

EXAMPLE 6

28% ammonia (5.3 g) and 90% formic acid (4.4 g) were mixed and the temperature was brought to 160° C by removal of water. To this mixture, 1-[5-(10,11-dihydro-5H-dibenzo[a,d]cycloheptenyl)]-3-carboxaldehyde-azetidine (4.8 g) was added, and the above-indicated temperature was maintained for 4 hours. 20% hydrochloric acid (40 ml) was then added and refluxed for 2 hours. The mixture was basified with 20% sodium hydroxide, extracted with benzene, washed repeatedly with water, dried (Na$_2$SO$_4$) and a solution of 7% ethanolic hydrochloric acid was added, so precipitating 1-[5-(10,11-dihydro-5H-dibenzo[a,d]cycloheptenyl)]-3-aminomethyl-azetidine dihydrochloride (1.4 g; m.p. 135°-140° C).

The compound 1-[5-(10,11-dihydro-5H-dibenzo[a,d]cycloheptenyl)]-3-carboxaldehyde-azetidine used as starting material was prepared as follows:

To a solution of 1-[5-(10,11-dihydro-5H-dibenzo[a,d]cycloheptenyl)]-3-cyano-azetidine (2.74 g) prepared according to Example 5, in anhydrous toluene (40 ml), a toluene solution of diisobutylalluminium hydride (1.42 g) at 0° C was added dropwise. This temperature was maintained for two hours, then an excess of a solution of 2N isopropanol in toluene was added, and the temperature was allowed to rise to room temperature. Few drops of water, then 1N hydrochloric acid (50 ml) were added and stirred for 15 minutes. After basification with 20% sodium hydroxide, the organic phase was separated and the aqueous phase was extracted with ethyl ether two times, 20 ml each time. The collected organic phases were washed with water, dried (Na$_2$SO$_4$) and evaporated to dryness, thus remaining a clear oil which gradually solidified to give 1-[5-(10,11-dihydro-5H-dibenzo[a,d]cycloheptenyl)]-3-carboxyaldehyde-azetidine.

EXAMPLE 7

To a solution consisting of 1-[5-(10,11-dihydro-5H-dibenze[a,d]cycloheptenyl)]-3-ethoxycarbamoylmethyl-azetidine (1 g) in anhydrous ethyl ether (70 ml), lithium alluminium hydride (0.34 g) in ethyl ether (10 ml) was added dropwise. The mixture was refluxed overnight, decomposed with water (0.35 ml), 15% sodium hydroxide (0.35 ml) and water (0.5 ml), then extracted with ethyl ether (3 × 50 ml). The ether was exhaustively extracted with 1N hydrochloric acid. The acid extracts were basified with 20% sodium hydroxide and reextracted with ethyl ether (2 × 50 ml). After drying over $Na_2SO_4$, 1-[5-(10,11-dihydro-5H-dibenzo[a,d]cycloheptenyl)]-3-methylaminomethyl-azetidine dihydrochloride (0.6 g; m.p. 100°–120° C) was precipitated with a solution of 7% ethanolic hydrochloric acid.

The compound 1-[5-(10,11-dihydro-5H-dibenzo[a,d]-cycloheptenyl)]-3-ethoxycarbamoylmethyl-azetidine, used as starting material, was prepared as follows: To a solution consisting of 1-[5-(10,11-dihydro-5H-dibenzo[-a,d]cycloheptenyl)]-3-aminomethyl-azetidine (1.4 g) dihydrochloride, prepared according to Example 6, in chloroform (16 ml), 2N sodium hydroxide (7.2 ml) was added cold. After cooling at 0° C, ethyl chloroformate (0.61 ml) in chloroform (3 ml) was added therein. After stirring for ten minutes, washing with water, drying ($Na_2SO_4$) and evaporation to dryness, crystallization with isopropyl ether gave 1-[5-(10,11-dihydro-5H-dibenzo[a,d]cycloheptenyl)]-3-ethoxy-carbamoylmethyl-azetidine (1.3 g; m.p. 103°–108° C.).

EXAMPLE 8

To a solution of 1-[5-(10,11-dihydro-5H-dibenzo[a,d]-cycloheptenyl)]-3-mesiloxymethyl-azetidine (2.5 g) in dimethylformamide (12 ml), 35% methylamine (15 ml) was added. The solution was kept at 40° C for 10 hours, then poured into water (120 ml) and extracted with ethyl ether (2 × 50 ml). Drying over sodium sulphate gave 1-[5-(10,11-dihydro-5H-dibenzo[a,d]cycloheptenyl)]-3-methylaminomethyl-azetidine (1.6 g).

Analogously, the following compounds were prepared:
1-[5-(10,11-dihydro-5H-dibenzo[a,d]cycloheptenyl)]-3-aminomethyl-azetidine
1-[5-(10,11-dihydro-5H-dibenzo[a,d]cycloheptenyl)]-3-dimethylaminomethyl-azetidine
1-[5-(10,11-dihydro-5H-dibenzo[a,d]cycloheptenyl)]-3-ethylaminomethyl-azetidine
1-[5-(10,11-dihydro-5H-dibenzo[a,d]cycloheptenyl)]-3-diethylaminomethyl-azetidine
1-[5-(10,11-dihydro-5H-dibenzo[a,d]cycloheptenyl)]-3-cyclohexylaminomethyl-azetidine
1-[5-(10,11-dihydro-5H-dibenzo[a,d]cycloheptenyl)]-3-isopropylaminomethyl-azetidine
1-[5-(10,11-dihydro-5H-dibenzo[a,d]cycloheptenyl)]-3-benzylaminomethyl-azetidine
1-[5-(10,11-dihydro-5H-dibenzo[a,d]cycloheptenyl)]-3-propargylaminomethyl-azetidine,
and the corresponding derivatives of formula (I) wherein Y is methoxy, fluorine, chlorine, trifluoromethyl, methylsulphonyl, and, besides, in an analogous way, starting from the following compounds:
1-[5-dibenzo[a,d]cycloheptenyl)]-3-mesiloxymethyl-azetidine
1-[6-(1,1a,6,10b-tetrahydro-dibenzo[a,e]cyclopropan[c]-cycloheptenyl)]-3-mesiloxymethyl-azetidine
1-[11-(6,11-dihydro-dibenzo[b,e]oxepinyl)]-3-mesiloxymethyl-azetidine
1-[11-(6,11-dihydro-dibenzo[b,e]thiepinyl)]-3-mesiloxymethyl-azetidine
1-{9-[9,10-dihydro-(10,10-dimethyl)-antracenyl]}-3-mesiloxymethyl-azetidine,
the following compounds were prepared:
1-[5-(5H-dibenzo[a,d]cycloheptenyl)]-3-methylaminomethyl-azetidine
1-[6-(1,1a,6,10b-tetrahydro-dibenzo[a,e]cyclopropan[c]-cycloheptenyl)]-3-methylaminomethyl-azetidine
1-[11-dihydro-dibenzo[b,e]oxepinyl)]-3-methylaminomethyl-azetidine
1-[11-(6,11-dihydro-dibenzo[b,e]thiepinyl)]-3-methylaminomethyl-azetidine
1-{9-[9,10-dihydro-(10,10-dimethyl)-antracenyl]}-3-methylaminomethyl-azetidine,
as well as all the other amino derivatives hereabove listed, and for each one of them, the corresponding derivatives of formula (I), wherein Y is fluorine, chlorine, methoxy, trifluoromethyl, methylsulphonyl.

The compound 1-[5-(10,11-dihydro-5H-dibenzo[a,d]-cycloheptenyl)]-3-mesiloxymethyl-azetidine used as starting material for the preparation of the compound 1-[5-(10,11-dihydro-5H-dibenzo[a,d]cycloheptenyl)]-3-methylaminomethyl-azetidine was prepared as follows:

Starting from 1-[5-(10,11-dihydro-5H-dibenzo[a,d]-cycloheptenyl)]-3-azetidinol, (34.3 g) prepared as described in Example 1, by adopting the technique described in J. Org. Chem. 37, 3953 (1972), 1-[5-(10,11-dihydro-5H-dibenzo[a,d]cycloheptenyl)]-3-carboxyazetidine (17 g) was obtained. Reduction with excess lithium alluminium hydride in tetrahydrofuran (300 ml) at reflux temperature for 12 hours gave, working up as usual, 1-[5-(10,11-dihydro-5H-dibenzo[a,d]cycloheptenyl)]-3-hydroxymethyl-azetidine (11.4 g).

By proceeding according to what described in Example 1, 1-[5-(10,11-dihydro-5H-dibenzo[a,d]cycloheptenyl)]-3-hydroxymethyl-azetidine (2 g) was converted into 1-[5-(10,11-dihydro-5H-dibenzo[a,d]cycloheptenyl)]-3-mesiloxymethyl-azetidine (2 g). The other compounds used as starting materials for the preparation of the compounds of the present Example were prepared analogously.

EXAMPLE 9

By proceeding analogously as described in Example 8, the compound 1-[5-(10,11-dihydro-5H-dibenzo[a,d]-cycloheptenyl)]-3-chloromethyl-azetidine was converted into 1-[5-(10,11-dihydro-5H-dibenzo[a,d]cycloheptenyl)]-3-methylaminomethyl-azetidine (yield = 75%)

The compound 1-[5-(10,11-dihydro-5H-dibenzo[a,d]-cyclopentyl)]-3-chloromethyl-azetidine used as starting material was prepared as follows:

To a solution consisting of 1-[5-(10,11-dihydro-5H-dibenzo[a,d]cycloheptenyl)]-3-hydroxymethyl-azetidine (2 g), prepared according to Example 8, in chloroform (20 ml), thionyl chloride (1.5 ml) in chloroform (3 ml) was added at 0° C. After the addition, the mixture was refluxed for four hours, then evaporated to dryness, taken up two times with benzene (2 × 30 ml) and evaporated to dryness again; the dihydrochloride of 1-[5-(10,11-dihydro-5H-dibenzo[a,d]cycloheptenyl)]-3-chloromethyl-azetidine (1.8 g) was crystallized from isopropanol/toluene. The dihydrochloride was suspended in water/ethyl ether (100 ml/100 ml) and a solution of 8% sodium hydroxide was added until the solution process was completed. The ethereal phase was separated, exhaustively washed with water, dried ($Na_2$-

SO$_4$) and evaporated to dryness to give 1-[5-(10,11-dihydro-5H-dibenzo[a,d]cycloheptenyl)]-3-chloromethyl-azetidine (1.2 g).

EXAMPLE 10

1-[5-(10,11-dihydro-5H-dibenzo[a,d]cycloheptenyl)]-2-methylaminocarbonyl-azetidine (3.1 g) was dissolved in anhydrous tetrahydrofuran (50 ml), and to this solution, lithium alluminium hydride (0.8 g) suspended in anhydrous tetrahydrofuran (20 ml) was added. The mixture was refluxed for 12 hours, then, after the addition of water (0.8 ml), 15% sodium hydroxide (0.8 ml) and water (2.4 ml), was filtered, washed with ethyl ether and evaporated to dryness. After taking up with ethyl ether (100 ml), washing with water and drying (Na$_2$SO$_4$), the hygroscopic 1-[5-(10,11-dihydro-5H-dibenzo[a,d]cycloheptenyl)]-2-methylaminomethyl-azetidine dihydrochloride (1.4 g; m.p. 110°–150° C) was precipitated with the addition of a 71 % ethanolic hydrochloride acid solution.

In an analogous way, the following compounds were prepared:

1-[5-(10,11-dihydro-5H-dibenzo[a,d]cycloheptenyl)]-2-aminomethyl-azetidine

1-[5-(10,11-dihydro-5H-dibenzo[a,d]cycloheptenyl)]-2-dimethylaminomethyl-azetidine 1-[5-(10,11-dihydro-5H-dibenzo[a,d]cycloheptenyl)]-2-ethylaminomethyl-azetidine 1-[5-(10,11-dihydro-5H-dibenzo[a,d]cycloheptenyl)]-2-diethylaminomethyl-azetidine 1-[5-(10,11-dihydro-5H-dibenzo[a,d]cycloheptenyl)]-2-cyclohexylaminomethyl-azetidine 1-[5-(10,11-dihydro5H-dibenzo[a,d]cycloheptenyl)]-isopropylaminomethyl-azetidine 1-[5-(10,11-dihydro-5H-dibenzo[a,d]cycloheptenyl)]-2-benzylaminomethyl-azetidine 1-[5-(10,11-dihydro-5H-dibenzo[a,d]cycloheptenyl)]-2-propargylaminomethyl-azetidine, and the corresponding derivatives of formula (I) wherein Y is methoxy, fluorine, chlorine, trifluoromethyl, methylsulphonyl, and besides, in an analogous way, starting from the following compounds:

1-[5H-dibenzo[a,d]cycloheptenyl)]-2-methylaminocarbonyl-azetidine

1-[6-(1,1a,6,10b-tetrahydro-dibenzo[a,e]cyclopropan[c]cycloheptenyl)]-2-methylaminocarbonyl-azetidine 1-[11-(6,11-dihydro-dibenzo[b,e]oxepinyl)]-2-methylaminocarbonyl-azetidine 1-[11-(6,11-dihydro-dibenzo[b,e]thiepinyl)]-2-methylaminocarbonyl-azetidine 1-{9-[9,10-dihydro-(10,10-dimethyl)-antracenyl]}-2-methylaminocarbonyl-azetine, the following compounds were prepared:

1-[5-5H-dibenzo[a,d]cycloheptenyl)]-2-methylaminomethyl-azetidine

1-[6-(1,1a,6,10b-tetrahydro-dibenzo[a,e]cyclopropan[c]cycloheptenyl)]-2-methylaminomethyl-azetidine 1-[11-(6,11-dihydro-dibenzo[b,e]oxepinyl)]-2-methylaminomethyl-azetidine 1-[11-(6,11-dihydro-dibenzo[b,e]thiepinyl)]-2-methylaminomethyl-azetidine 1-{9-[9,10-dihydro-(10,10-dimethyl)-antracenyl]}-2-methylaminomethyl-azetidine, as well as all the other amino derivatives hereabove listed, and for each one of them, the corresponding derivatives of formula (I), wherein Y is chlorine, fluorine, methoxy, trifluoromethyl, methylsulphonyl.

The compound 1-[5-(10,11-dihydro-5H-dibenzo[a,d]cycloheptenyl)]-2-methylaminocarbonyl-azetidine used as starting material for the preparation of the compound 1-[5-(10,11-dihydro-5H-dibenzo[a,d]cycloheptenyl)]-2-methylaminomethyl-azetidine dihydrochloride was prepared in the following way:

A solution consisting of 5-amino-10,11-dihydro-5H-dibenzo[a,d]cyclo-heptene (34.9 g) prepared according to Example 1, and α, γ-dibromo-methyl-butyrate (14.45 g) in acetonitrile (250 ml) was refluxed for 24 hours. After cooling, the solid product precipitated was filtered off, the remaining solution was evaporated, the residue taken up with ethyl ether (500 ml), then gaseous hydrochloric acid was bubbled. The solid product (14 g) was filtered, dissolved in water (300 ml) and extracted with ethyl ether (2 × 300 ml) after basification of the solution with 8% sodium hydroxide. The ethyl ether was washed with water and evaporated to dryness, thus remaining 1-[5-(10,11-dihydro-5H-dibenzo[a,d]cycloheptenyl)]-2-methoxycarbonyl-azetidine, as a clear oil (12 g).

1-[5-(10,11-dihydro-5H-dibenzo[a,d]cycloheptenyl)]-2-methoxycarbonyl-azetidine (9.2 g), prepared as described above, was kept for 12 hours at 60° C in a 35% methylamine aqueous solution (100 ml), then poured into water, extracted with ethyl acetate, washed with water to neutrality, evaporated to dryness, to give 1-[5-(10,11-dihydro-5H-dibenzo[a,d]cycloheptenyl)]-2-methylaminocarbonyl-azetidine (7.1 g; m.p. 75°–80° C).

The other compounds used as starting materials for the preparation of the compounds of the present Example were prepared analogously.

EXAMPLE 11

Starting from 1-[5-(10,11-dihydro-5H-dibenzo[a,d]cycloheptenyl]-2-(N-morpholinocarbonyl)-azetidine and following the technique described in Example 10, 1-[5-(10,11-dihydro-5H-dibenzo[a,d]cycloheptenyl]-2-(N-morpholinomethyl)-azetidine was obtained (yield 88%). The compound used as starting material was prepared as follows: 1-[5-(10,11-dihydro-5H-dibenzo[a,d]cycloheptenyl)]-2-methoxycarbonyl-azetidine (4.6 g), prepared according to Example 10, was dissolved in morpholine (30 ml) and kept at 50° C for 2 days, then poured into water. The precipitate was filtered, thoroughly washed with water, crystallized from toluene to give 1-[5-(10,11-dihydro-5H-dibenzo[a,d]cycloheptenyl]-2-(N-morpholinocarbonyl)-azetidine (3.6 g).

EXAMPLE 12

A solution consisting of 1-[5-(10,11-dihydro-5H-dibenzo[a,d]cyclo heptenyl)]-3-methylamino-azetidine (2.8 g), prepared according to Example 1, in acetic anhydride (50 ml) was allowed to rest for 12 hours at room temperature. By evaporation to dryness, grinding of the residue in ethyl ether, and crystallization from ethyl acetate, 1-[5-(10,11-dihydro-5H-dibenzo[a,d]cycloheptenyl)]-3-(N-methyl-N-acetyl)-azetidine (2.7 g) was obtained.

EXAMPLE 13

To a solution of N-methyl-acetamide (0.73 g) in anhydrous dimethyl formamide (10 ml), sodium hydride (0.26 g) was added. After stirring for 2 hours at room temperature in a nitrogen atmosphere, 1-[5-(10,11-dihydro-5H-dibenzo[a,d]cycloheptenyl)]-3-mesiloxy-azetidine (3.5 g), prepared according to Example 1, was added. The temperature was gradually brought to 50°

C, and this temperature was maintained for eight hours. The mixture was then poured into water (100 ml), extracted with chloroform (3 × 30 ml), repeatedly washed with water, dried (Na₂SO₄) and evaporated to dryness, to give 1-[5-(10,11-dihydro-5H-dibenzo[a,d]cycloheptenyl)]-3-(N-methyl-N-acetyl)-azetidine (1.6 g).

EXAMPLE 14

Starting from 1-[5-(10,11-dihydro-5H-dibenzo[a,d]cycloheptenyl)]-3-(N-methyl-N-acetyl)-azetidine (3.2 g), prepared according to Example 13, and following the technique described in Example 10, 1-[5-(10,11-dihydro-5H-dibenzo[a,d]cycloheptenyl)]-3-(N-methyl-N-ethyl)-amino-azetidine (1.6 g) was obtained.

We claim:

1. A compound of formula:

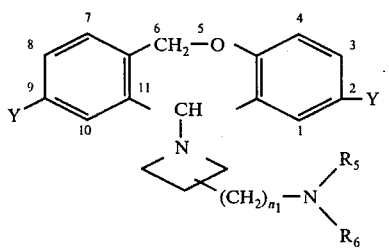

wherein:

$n_1$ is zero or 1

$R_5$ and $R_6$ each independently represent hydrogen or $C_1$-$C_6$ alkyl; and one of the Y groups is hydrogen and the other is hydrogen, halogen, $C_1$-$C_6$ alkoxy, trifluoromethyl or methylsulphonyl, provided that, when $n_1$ is zero, the

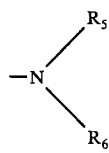

radical is exclusively bound to the carbon atom in the 3-position of the azetidine radical, and the salts thereof with pharmaceutically acceptable acids.

2. 1-[11-(6,11-dihydro-dibenzo[b,e]oxepinyl)]-3-methylamino-azetidine, as claimed in claim 1.

3. 1-[11-(2-chloro-6,11-dihydro-dibenzo[b,e]oxepinyl)]-3-methylamino-azetidine, as claimed in claim 1.

4. 1-[11-(9-chloro-6,11-dihydro-dibenzo[b,e]oxepinyl)]-3-methylamino-azetidine, as claimed in claim 1.

5. 1-[11-(2-trifluoromethyl-6,11-dihydro-dibenzo[b,e]oxepinyl)]-3-methylamino-azetidine, as claimed in claim 1.

6. 1-[11-(9-trifluoromethyl-6,11-dihydro-dibenzo[b,e]oxepinyl)]-3-methylamino-azetidine, as claimed in claim 1.

7. 1-[11-(2-methoxy-6,11-dihydro-dibenzo[b,e]oxepinyl)]-3-methylamino-azetidine, as claimed in claim 1.

8. 1-[11-(9-methoxy-6,11-dihydro-dibenzo[b,e]oxepinyl)]-3-methylamino-azetidine, as claimed in claim 1.

9. 1-[11-(2-methylsulphonyl-6,11-dihydro-dibenzo[b,e]oxepinyl)]-3-methylamino-azetidine, as claimed in claim 1.

10. 1-[11-(9-methylsulphonyl-6,11-dihydro-dibenzo[b,e]oxepinyl)]-3-methylamino-azetidine, as claimed in claim 1.

11. 1-[11-(6,11-dihydro-dibenzo[b,e]oxepinyl)]-3-methylaminomethyl-azetidine, as claimed in claim 1.

12. 1-[11-(6,11-dihydro-dibenzo[b,e]oxepinyl)]-2-methylamino-methyl-azetidine, as claimed in claim 1.

13. A method of treating central nervous system depression consisting essentially of administering to a person suffering therefrom an effective amount of compound 1-[11-(6,11-dihydro-dibenzo[b,e]oxepinyl)]-3-methylamino-azetidine, and the pharmaceutically acceptable salts thereof.

14. The method of claim 13 wherein from 20 to 50 mg. of the compound is administered 2-4 times a day.

15. An anti-convulsant pharmaceutical composition containing, as the active ingredient thereof, an effective amount of a compound of claim 1, together with a suitable carrier or diluent.

16. A method of treating convulsions consisting of administering to a person suffering therefrom an effective amount of a compound of claim 1.

* * * * *